(12) United States Patent
Hartung (10) Patent No.: US 6,230,061 B1
(45) Date of Patent: May 8, 2001

(54) ELECTRODE ARRANGEMENT

(75) Inventor: Wolfgang Hartung, Magdeburg (DE)

(73) Assignee: Biotronik Mess—und Therapiegerate GmbH & Co. Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/142,085
(22) PCT Filed: Mar. 3, 1997
(86) PCT No.: PCT/DE97/00520
  § 371 Date: Jan. 27, 1999
  § 102(e) Date: Jan. 27, 1999
(87) PCT Pub. No.: WO97/31678
  PCT Pub. Date: Sep. 4, 1997

(30) Foreign Application Priority Data
  Mar. 1, 1996 (DE) .............................................. 196 09 471

(51) Int. Cl.$^7$ ....................................................... A61N 1/05
(52) U.S. Cl. .............................................................. 607/122
(58) Field of Search .................................. 607/122, 123, 607/119, 9

(56) References Cited

U.S. PATENT DOCUMENTS

3,903,897  9/1975  Woollons et al. .
5,172,694  12/1992  Flamming et al. .

*Primary Examiner*—Scott M. Getzow
(74) *Attorney, Agent, or Firm*—Venable; George H. Spencer; Robert Kinberg (57) ABSTRACT

An electrode arrangement for stimulating the heart by means of the following elements: an implantable cardiac pacemaker which generates electrical pulses; a first electrode (11) connected to a first output of the pacemaker and mounted on an electrode line (10) fitted intracardially and not attached to the heart wall (i.e., floating); and a second electrode (12) for transmitting the electrical stimulation pulses to the excitable heart tissue, situated on the electrode line away from the first electrode and connected to a second pacemaker output. The voltage pulses at the two electrodes have differing polarities relative to another electrode and the electrodes (11, 12) are arranged on the electrode line in such a way that the electrical dipole field which forms is distorted towards the stimulation point in such a way that a raised potential gradient above the stimulus threshold is formed there.

22 Claims, 5 Drawing Sheets

ELECTRODE ARRANGEMENT

BACKGROUND OF THE INVENTION

The invention relates to an electrode arrangement for stimulating the heart by mans of an implantable cardiac pacemaker which generates electrical pulses.

In the treatment of various chronic disturbances in cardiac rhythm, implanted cardiac pacemakers are in use, in conjunction with stimulating electrodes disposed on an intracardial electrode catheter and positioned on the inner wall of the heart; the stimulatable cardiac tissue is excited by way of these electrodes. The design of the pacemakers and the associated electrode lines has undergone increasing perfection, and numerous technical solutions have been found for anchoring the electrode catheters to the heart wall—both in the ventricle and in the atrium-and substantial practical improvements have in fact successfully been attained.

Nevertheless, even today, electrode dislocations, which lead to a worsening of contact with the stimulatable tissue on the inner wall of the heart, or even a loss of such contact, and consequently at least a substantial increase in the stimulation threshold and thus increased current consumption by the pacemaker and reduced service life, and in the worst case cause the pacemaker to become nonfunctional, are among the most important complications in pacemaker therapy.

In addition, the fact that up to the present the stimulating pulses of an implanted pacemaker are transmitted to the stimulatable muscle tissue of the inner wall of the heart in the lower region of the ventricle or atrium are transmitted via electrodes attached to the walls is also necessarily unsatisfactory, for fundamental physiological reasons.

Floating electrodes, on the other hand, have been unable so far to assure stimulation with sufficient safety that regular use would be appropriate.

SUMMARY OF THE INVENTION

It is therefore the object of the invention to disclose an improved electrode arrangement of the generic type defined at the outset, which enables operation of a cardiac pacemaker that better suits physiological conditions with regard to localization of the stimulating pulses and is thus more reliable.

This object is attained by an electrode arrangement, according to the invention, in which a first electrode is connected to a first output of a cardiac pacemaker and is disposed on an intracardially placed electrode line and a second electrode, spaced apart from the first electrode on the electrode line, is connected to a second output of the cardiac pacemaker where the first and second electrode transmit electrical stimulating pulses up to a stimulation threshold to cardiac tissue wherein a third electrode is disposed so that the voltage pulses at the first and second electrodes have a different polarity from the third electrode and the first and second electrodes are disposed on the electrode line in such a way that the electrical dipole field that develops is distorted in the direction of the stimulation site such that an elevated potential gradient develops above the stimulation threshold.

The invention encompasses the concept of achieving an electrode arrangement and electrode triggering with which the stimulating pulses of the pacemaker can be delivered to the region that rank highly, in the hierarchy of impulse formation, in the impulse-forming and conduction system of the heart—primarily the sinoatrial node and secondarily the AV node-so that a sinoatrial node syndrome, for instance, can be treated directly where it occurs, or in the case of an AV block, stimulation can be done directly in the region primarily affected by this physiological defect.

For practical application of this concept, the proposed electrode arrangement makes use of the means of "focusing" of the electrical field, which develops in the surroundings of two or more electrodes in a suitable geometrical electrode arrangement when stimulating pulses of opposite polarity are output simultaneously, on the sinoatrial node or the AV node or other region to be stimulated.

In this way it is possible, even with a floating electrode, to concentrate such a strong electrical stimulus effect locally that physical contact between the tissue and the stimulating electrode is not required.

It is also of particular importance for the invention that not only the absolute potential course but also the field gradient in the region of the tissue should attain the highest possible value. This means that a maximum curvature in the equipotential lines in the region of the tissue to be stimulated should be attained, if at all possible in such a way that the equipotential lines enter the tissue and emerge from it again in the stimulation region. This can be attained by a geometric dimensioning in such a way that the electrode is dimensioned such that the equipotential line or plane is located on the side opposite the pacemaker. The pacemaker housing, as an indifferent electrode, in this case effects an additional strong distortion of the dipole field in the manner described. This effect is promoted by the discontinuity in the potential line course in the transitional region between tissue and blood, because of the lower specific resistance in the blood.

Elevating the potential gradient by the suitable geometric electrode arrangement on the one hand and the opposite polarity of the pulses on the other makes it possible to exceed the stimulation threshold in tissue regions not directly adjacent the electrodes, and thus makes it possible to stimulate the target regions for the excitement, namely the sinoatrial node or AV node, which are not located on the surface of the heart wall and thus are in regions of the heart where a fixation of electrodes is practically impossible.

In an embodiment of the electrode arrangement which is especially advantageous with regard to controlling the target excitation region, the electrode arrangement includes at least one third electrode, in a spatial relationship with the first and second electrodes, which is embodied and disposed and acted upon by a predetermined third voltage in such a way that in the region of the sinoatrial node or the AV node, it elevates the potential gradient above the value attainable solely with the first and second electrodes (for a given predetermined voltage amplitude).

In an embodiment that can advantageously be constructed in the conventional way and is favorable for implanting, the second electrode and/or the further electrode or electrodes are disposed in the intracardially placed electrode line.

This electrode line expediently has a length and/or curvature dimensioned such that the electrodes after introduction into the heart are disposed in the region of the roof of the atrium near the abouchement of the superior vena cava or near the septum and the abouchement of the coronary sinus into the atrium, that is, are disposed a slight distance from them, depending on whether the sinoatrial node or the AV node is to be excited.

In a preferred feature, the electrode line is embodied such that the third and/or further electrode or electrodes are disposed above the first and second electrodes, in particular approximately on the extended straight line connecting them—in the case where the sinoatrial node is stimulated, especially in the superior vena cava.

If in the aforementioned feature a third electrode is provided, then it is disposed essentially at the apex of curvature of the electrode line, such that it is spaced apart from a straight connecting line between the first and second electrodes.

Since it is unnecessary to fix the electrode line to the heart wall in the electrode arrangement of the invention, the electrode line can "float" in the heart. Thus it is accordingly constructed expediently with a flexural strength, and optionally a preimposed curvature in the longitudinal course, such that the electrodes after introduction into the heart are essentially not in direct contact with the heart wall but rather are disposed near the region to be stimulated.

In a preferred version, the electrode line has a branching point—which in an especially variable version is even still displaceable after introduction-and the second or a further electrode is disposed on a segment of the electrode line that branches off from the main line, while at least two electrodes (including the first one) are disposed on the main line.

With this version, a similar result is obtainable as when a curvature and a third electrode in the region of the apex of curvature are provided, namely a deformation of potential lines in the direction of the target region. With the aid of a branching point, this displacement can be better controlled three-dimensionally than with a single-strand electrode line.

The curvature, or the offset of the segment of the electrode line branching off from the main line, is generated by suitable means (known per se) after introduction, preferably for instance by elements made of a memory alloy activated at body temperature, or prestressed elements which when a guide wire used for the introduction is removed from the electrode line assume a preimpressed form. It is also possible to provide means for varying the curvature from outside.

An improved possibility for moving the electrodes toward the tissue region to be affected, as compared with electrode lines with an electrode configuration that is symmetrical with respect to the center axis, is offered by a version in which the electrodes are disposed asymmetrically on the electrode line with respect to a center line thereof. Some of the electrodes may be disposed on one side of the line and others on the opposite side, but it can also be expedient to dispose all the electrodes on the same side of the line.

In another preferred version, the third (or a further) electrode is embodied as a planar electrode located outside the heart, in particular as a pacemaker housing that receives the voltage source and the cardiac pacemaker; this pacemaker is especially connected as an indifferent electrode, that is, is connected to zero potential.

The electrode line can preferably have at least one group of four axially spaced-apart electrode segments, and the first voltage pulse is applied to the first and third or to the second and fourth electrode segments of the group, so that a first electrical dipole field builds up between these segments, and the second pulse is applied to the remaining electrode segments of the group, so that a second dipole field spatially offset from the first dipole field builds up between these electrode segments.

In particular, the electrodes of different polarity are disposed in such a way on the electrode line, and/or the ratio of the potentials is selected such, that the resultant equipotential lines (and thus essentially the field lines as well) enter the heart wall and emerge from it again at the stimulation site.

For these or other embodiments, in which a plurality of electrode groups are to be triggered in pulsed fashion, expediently two (or more) pulse generators are provided in the cardiac pacemaker, which can each essentially simultaneously generate both a first and a second voltage pulse of opposite polarity.

BRIEF DESCRIPTION OF THE DRAWINGS

Other advantageous features of the invention are defined by the dependent claims and will be described in further detail below in conjunction with the description of the preferred embodiment of the invention based on the drawings in which:

DETAILED DESCRIPTION OF THE INVENTION

Figure 1:
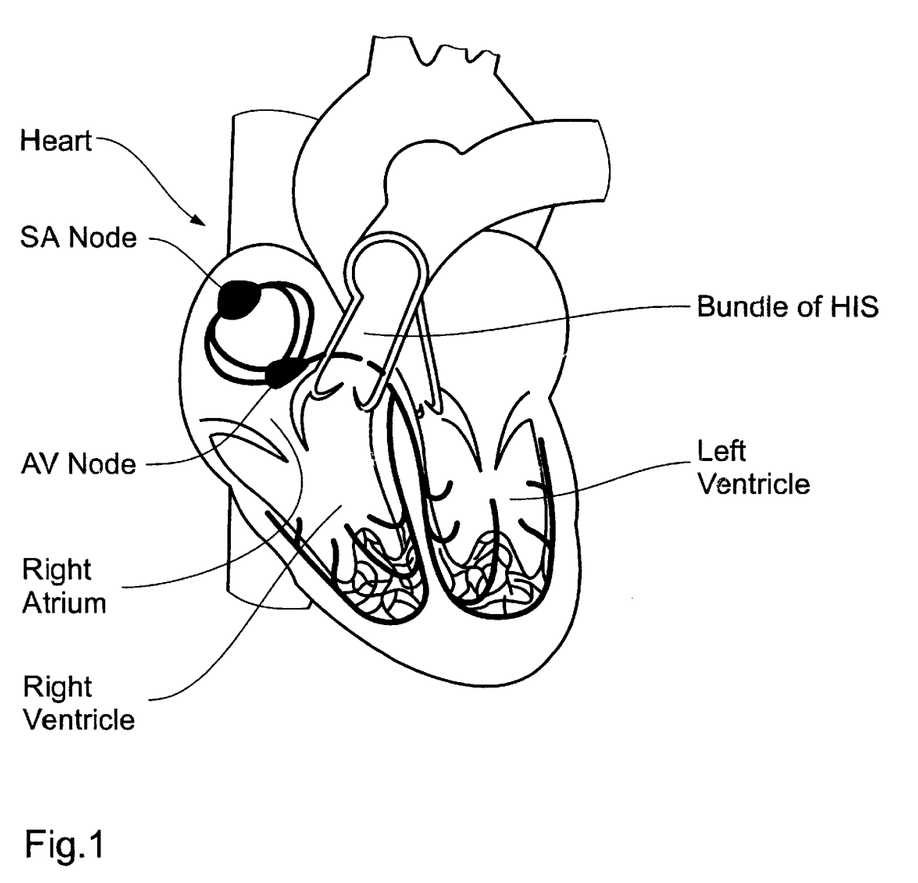
FIG. 1 is a schematic illustration of the impulse-forming and electrical conduction system of the heart.

The location of the elements of the impulse-forming and electrical conduction system in the heart (to which the bundle of His, not mentioned above, and the left and right bundle branch—each debouching into the Purkinje fibers-belong) is first shown in sketchlike form in FIG. 1.

Figure 2:
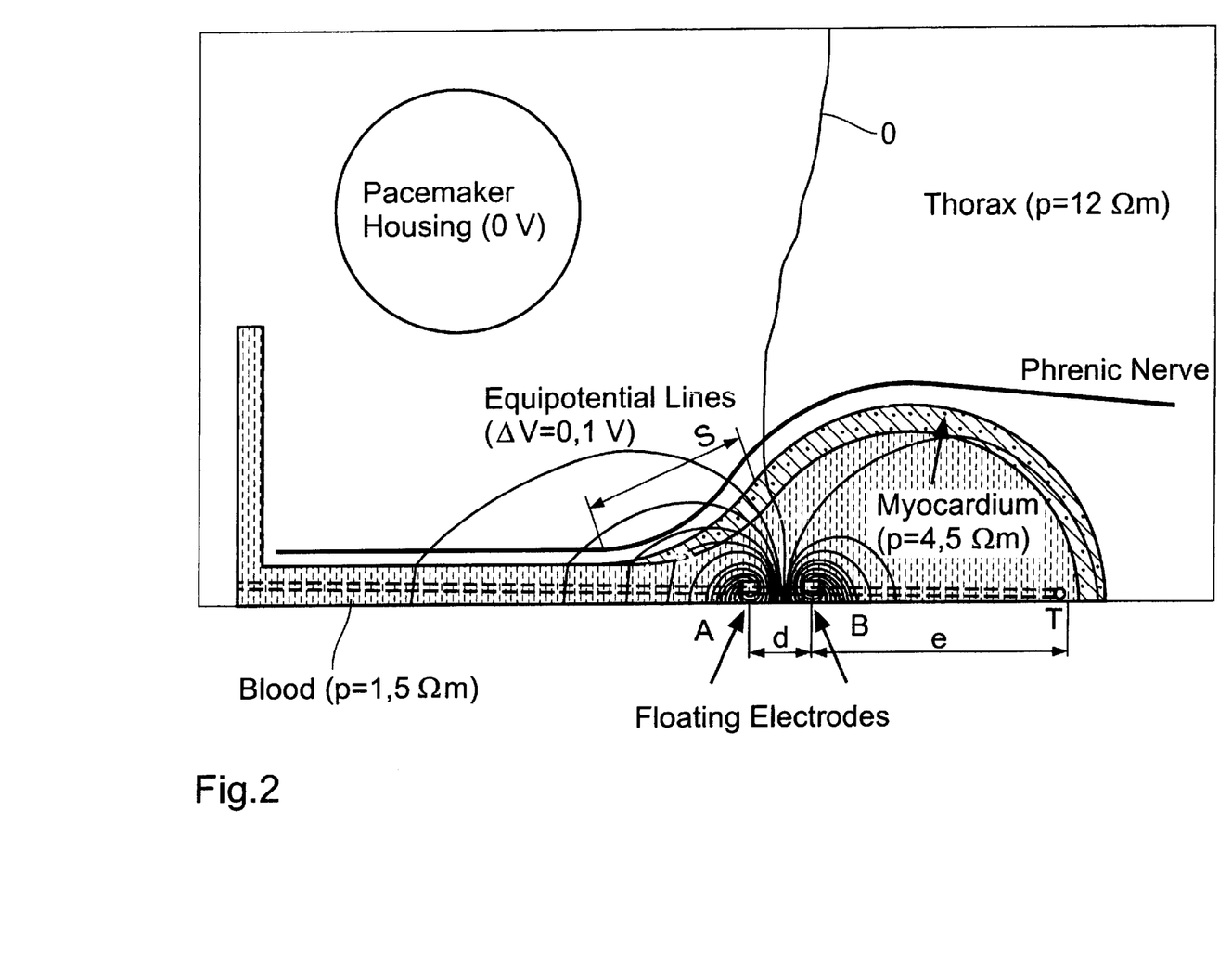
FIGS. 2 and 2a–2d shows schematic illustrations of the field line course for various electrode arrangements to explain a fundamental concept of the invention, including activation functions.

FIG. 2 schematically shows the course of field lines in an electrode arrangement, to explain a fundamental concept of the invention. The field lines shown are not intended to simulate the field intensity to scale but instead are chosen to make certain relationships in the field geometry clear.

In the schematic illustration, the distribution of blood and tissue in the atrium and the adjacent "superior vena cava" are shown. Also shown is the myocardium of the atrium and the phrenic nerve and the surrounding thorax. A third electrode-in this case the pacemaker housing-is at the potential of 0 V, even in the stimulation situation. The floating electrode line (shown in dashed lines) carries the electrodes A and B, which form an electrical dipole; in the present example, the electrode A is polarized negatively (−1.5 V) and the electrode B is polarized positively (+1.5 V) compared to the pacemaker housing. It can be seen that in the electrode position shown, the potential line of 0 V (pointing nearly straight upward in the drawing) causes a deformation toward the third electrode (pacemaker housing).

The specific resistances are also given in FIG. 1. It can also be seen that if the pacemaker housing is considered to be an ideal conductor (equipotential at 0 V) for the electrode position shown, a maximally curved course of the potential lines occurs in the stimulation region. In this way, the steepest possible potential gradient is attained in the region of the heart muscle, and the equipotential lines that penetrate the myocardium leave the wall of the myocardium again in the immediate vicinity of the penetration point.

This is attained by the electrode geometry shown in FIG. 1, which is determined by the spacing, or distance, d between the electrodes and the distance e from the electrodes to the end of the electrode that is located in the apex of the heart and that in the exemplary embodiment shown has a conventional (unipolar) ventricle electrode T. The distance e is referred in the example shown to the center of the distance d between the two electrodes A and B. Depending on the size of the human heart, the magnitude e can vary; in many cases, maximum stimulation effectiveness can be attained simply by suitable positioning. The distance d is selected such that a region of maximum curvature penetrates the stimulation region S. Here greater spacing reduces the curvature. An overly small spacing, conversely, does not permit the field region of maximally curved equipotential lines to reach the stimulation region. To this extent, an optimal stimulation effect may possibly be attained by trial and error.

A further variable in the diagram is the symmetry of the voltage at the electrodes A and B. By increasing the potential of electrode B, the indifferent potential line 0 V can also be shifted into the region to be stimulated. However, in comparison to the geometrical variables, this effect has a relatively lesser influence, but it is important with respect to the proportion of stimulation of myocardial fiber and the phrenic curve, as will be discussed in further detail hereinafter.

With the electrode geometry schematically shown in the diagram, the described potential distribution can be well attained in the inlet region of the superior vena cava toward the atrium. It can be seen in FIG. 2 that in the region S, the curvature of the equipotential lines is so great that even the field lines extending at right angles to them enter the heart wall and emerge again in the stimulation region. The stimulation region is thus distinguished by a zone in which the field intensities generated are at a maximum.

Figure 2A:
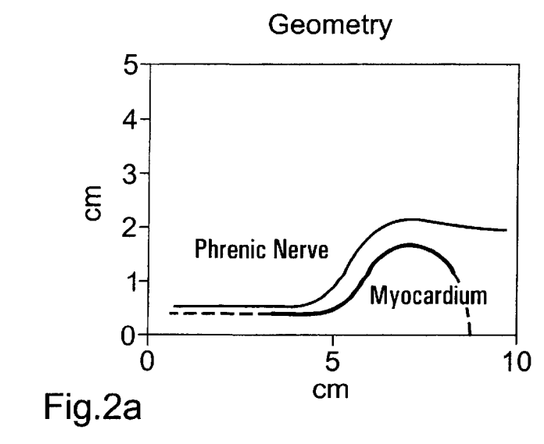

In FIGS. 2a–d, the influence on the stimulation of heart muscle cells and the phrenic nerve that results from the electrical pulse symmetry is shown. FIG. 2a, in a simplified model geometry, shows the relative course of the phrenic nerve in the myocardium. The phrenic serve can be thought of as one continuous nerve strand, and its excitability has a characteristic course that will be discussed in further detail hereinafter.

Figure 2B:
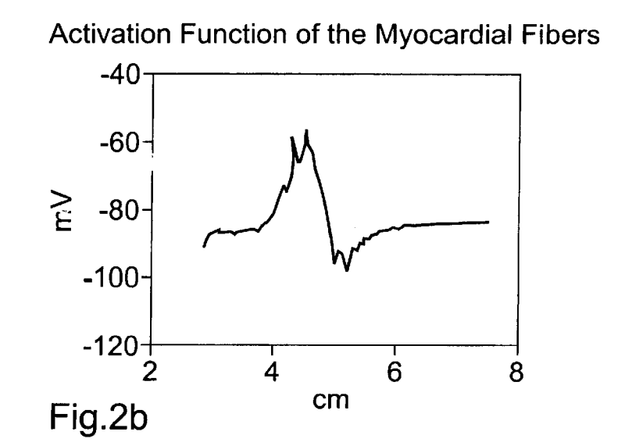
Figure 2C:
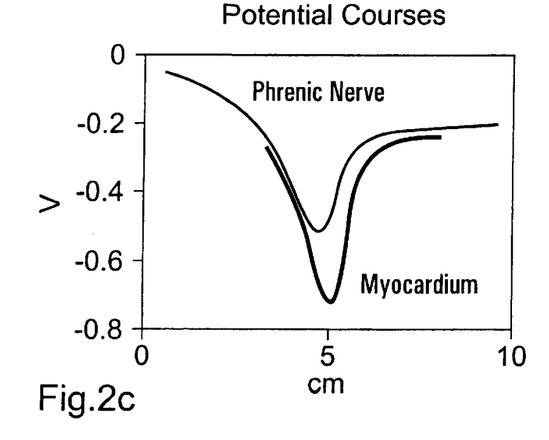
Figure 2D:
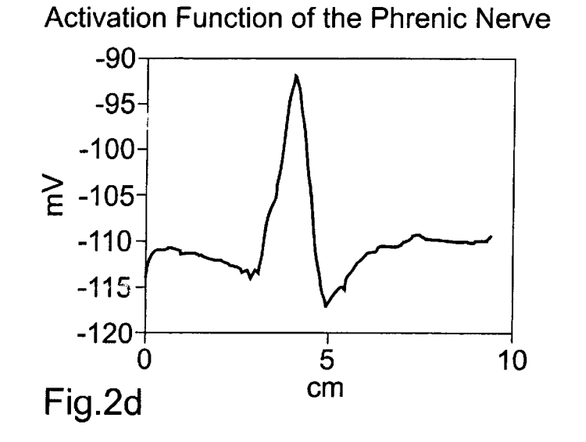

The activation function of the myocardial fiber is shown in further detail in FIG. 2b. It is located at −90 mV. A muscle fiber that extends from the abouchement of the superior vena cava into the atrium as far as the level of the valve is considered to be a component of the myocardium. The resting membrane potential and the stimulation threshold are −90 mV and −60 mV, respectively. The stimulation of the myocardial fiber takes place above the threshold.

In a pacemaker stimulation of the heart, the problem arises of avoiding excitation of the phrenic nerve, because stimulating it causes undesired twitching of the diaphragm or of the pocket of the pacemaker.

In contrast to heart muscle cells, nerve cells have a resting membrane potential of about −110 mV. The stimulation threshold is approximately −90 mV and thus is below the threshold.

To assure that the myocardial fibers will be stimulated above the threshold but the nerve cells will not, in the pacemaker electrode shown here the "signal to noise ratio" between the desired myocardial stimulation and the undesired phrenic nerve stimulation is optimized at the same time. This is achieved by means of the selected asymmetry of the electrode potentials A and B. Based on a total voltage of 3 V and on the goal of stimulating the myocardium as safely as possible on the one hand and on the other of as much as possible avoiding or minimizing the phrenic nerve stimulation at the same time, the illustration shown in FIG. 2b results for the potential courses, with an electrical pulse voltage of −2.55 V for electrode A and an electrical pulse voltage of +0.45 V of electrode B. The asymmetry factor in this (model) instance is 1.7/0.3. This assumes rectangular pulses, which are output in-phase, that is, chronologically synchronously without any offset.

This optimum differs from one patient to another and can be attained by individual programming in accordance with which the electrode is placed in the heart. Care must be taken that the myocardium and phrenic nerve not be located in the same plane. The signal-to-noise ratio that actually results is accordingly far better than the theoretical value calculated here for a two-dimensional model. It must be noted that according to the invention, focusing on the myocardial stimulation must be done first. After that, by varying the symmetry of the pulses, the attempt can be made to eliminate any possibly perceived disturbing stimulation of the phrenic nerve by reprogramming the symmetry and thus "fading it out".

Figure 3:
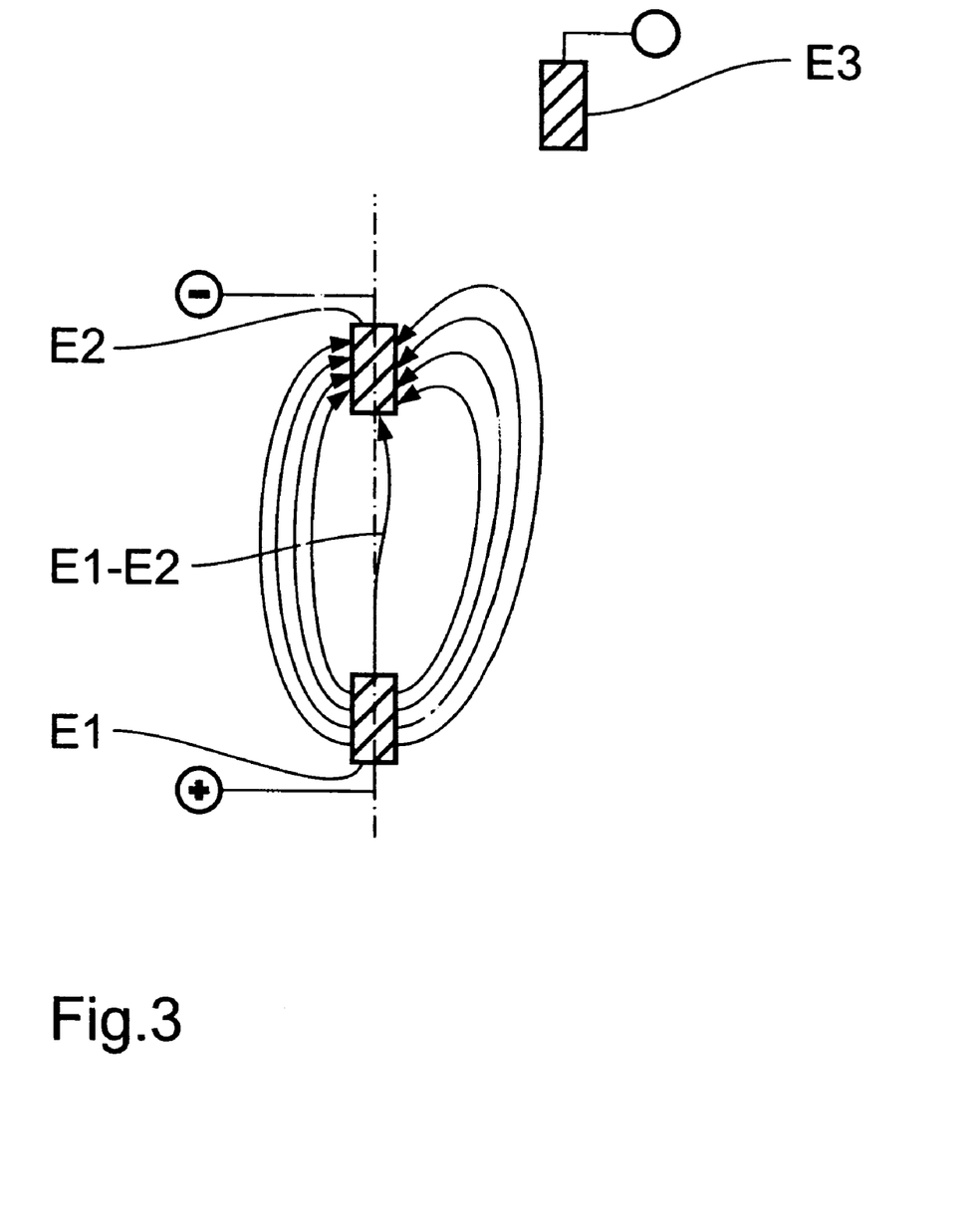
FIG. 3 shows a further schematic illustration of the course of the electrical field in a further version of the invention.

In FIG. 3, the electrical field that develops between two electrodes E1 and E2, connected to the positive pole "+" and the negative pole "−" of a voltage source, respectively, with small dimensions (in open space) relative to their spacing is shown. This is approximately equivalent to the field between two spot charges with different signs. The potential gradient is greatest on the straight connecting line E1–E2 between the two electrodes E1 and E2, and the field intensity and thus the potential gradient as well decreases in a first approximation in accordance with Coulomb's Law with increasing distance from this line. Instead of the equipotential lines, the deformed electrical field lines here are shown; they are always oriented at right angles to the equipotential lines.

As can be seen, a similar effect, which however is asymmetrical with regard to the connecting line E1–E2 between the first and second electrodes E1, E2, occurs if a third electrode E3" is placed at a distance from the extended connecting line E1–E2. In the half-space remote from the third electrode, the effective range of the field has decreased—again assuming equal voltages to those of the other drawings-while in the half-space toward it it has expanded. It can be seen that in the region of the electrode E2, which is toward the electrode E3, pronounced distortion of the field lines—in the direction toward E3-has occurred. If the heart wall takes a course shown in dashed lines and marked W in FIG. 3, then the field lines enter this heart wall and emerge from it again in the stimulation region S.

Similar effects, which can be calculated by one skilled in the art on the basis of the principles of electrostatics, occur with different electrode polarities and spatial electrode arrangements, and the specific field line patterns naturally also depend on the quantitative values of the voltages applied.

The conditions sketched and explained above also apply approximately-as experiments have confirmed-to electrode lines and electrode catheters (known per se) with insulating sheathing and with a plurality of electrode segments spaced apart from and insulated from one another, and they apply in particular also to electrode arrangements in a physiological fluid.

Because it is possible to place electrode catheters in floating fashion essentially rectilinearly in the heart, many configurations can be arrived at with which the invention is realized and the sinoatrial node or the AV node is excited directly via a sufficiently strong electrical field generated in its surroundings.

Some examples of this will now be given, but they are not to be take as a limitation of the invention.

Figure 4A:
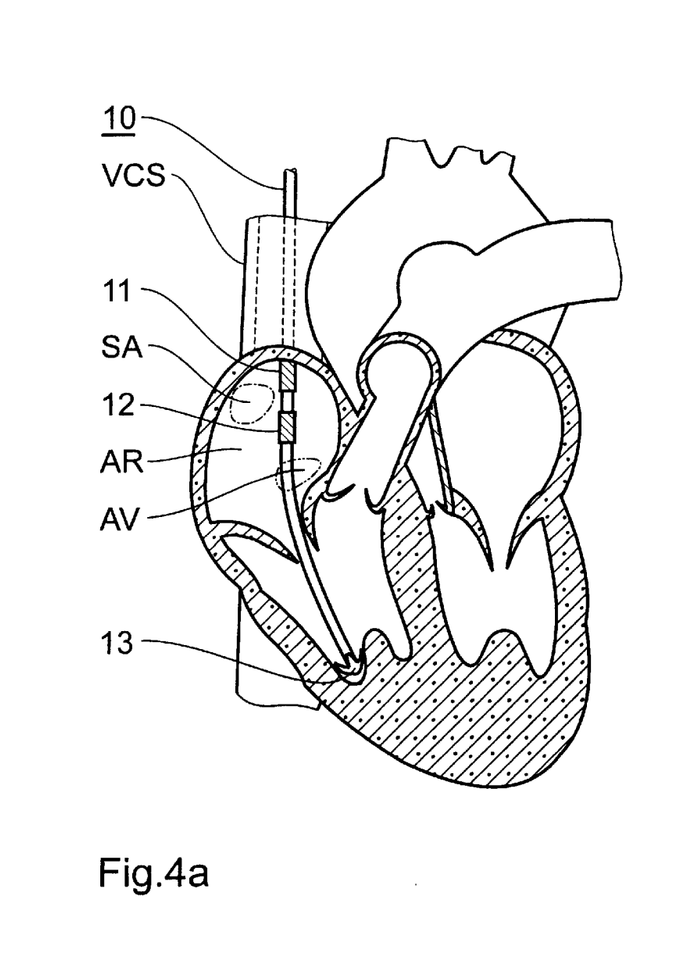
FIGS. 4a and 4b are schematic illustrations of electrode arrangements in accordance with a further embodiment of the invention (in two variants).
Figure 4B:
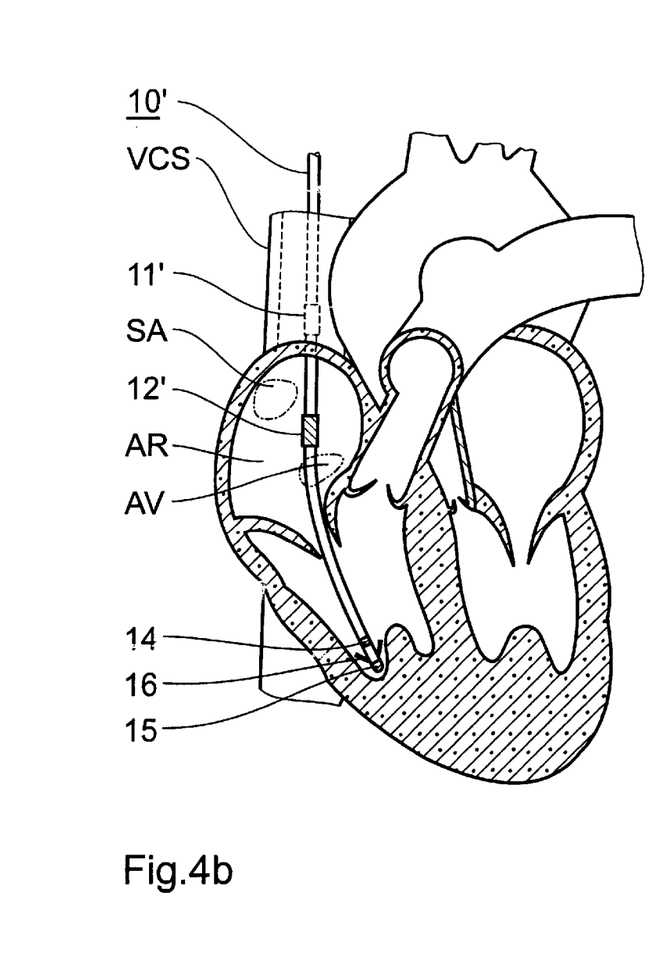

FIGS. 4a and 4b schematically show two electrode lines 10 and 10', placed floating with a rectilinear course along the superior vena cava VCS in the right atrium AR of a heart H, on each of which lines two electrodes (or segments thereof) 11 and 12, and 11' and 12', respectively, are formed. Both lines are embodied in their length and in the spacing of the electrodes 12 and 13, and 12' and 13', respectively, in such a way, and are placed so far in the atrium, that in bipolar operation, that is, when a voltage with different polarity is applied, they can excite the sinoatrial node SA without having to be fixed to the wall or even positioned.

The electrodes shown in the two drawing figures are suitable for two-chamber operation. In FIG. 4*a*, a conventional ventricle electrode 13 with fixation means on the end of the electrode line is provided. In FIG. 4*b*, a corresponding electrode is provided, which on its free end in the ventricle has a likewise floating pair of electrodes 14 and 15. These electrodes are dimensioned like the atrium electrodes in accordance with suitable geometrical principles and are oriented toward the endocardium of the ventricle but without being firmly anchored there. In their end region, they have thin tines 16 of elastic material, which are recessed relative to the end of the electrode and do not have the task of fixing the end of the electrode to this stimulation electrodes in the vicinity of the tissue but rather are intended to serve only to keep the end of the electrode centered approximately in the middle cross section of the chamber in the vicinity of its lower end.

It can be seen that the inventive effect can also be attainable with a plurality of electrodes. For instance, two electrodes may be disposed in the atrium, but a further electrode can also be located in the superior vena cava. Whether one or the other electrode arrangement is used is dependent on the actual location of the sinoatrial node in a given patient and on its stimulation threshold.

In its realization, the invention is not limited to the preferred exemplary embodiment described above. On the contrary, a number of variants are conceivable that make use of the embodiment shown even in fundamentally differently designed versions.

What is claimed is:

1. An electrode arrangement for stimulating the heart by means of an implantable cardiac pacemaker for generating electrical pulses, comprising:

a first electrode adapted for connection to a first output of the cardiac pacemaker and disposed on an intracardially placed electrode line that is not located on a wall of the heart;

a second electrode, spaced apart from the first electrode on the electrode line and adapted to connection to a second output of the cardiac pacemaker, for transmitting the electrical stimulating pulses to stimulatable cardiac tissue at a stimulation site; and a third electrode, wherein voltage pulses at the first and second electrodes have a different polarity from the third electrode, and the first and second electrodes are disposed on the electrode line in such a way that the electrical dipole field that develops is distorted in the direction of the stimulation site such that an elevated potential gradient above the stimulation threshold develops there.

2. The electrode arrangement of claim 1, wherein the electrodes of different polarity are disposed on the electrode line in such a way, and/or the ratio of the potentials is selected in such a way, that the resultant equipotential lines are curved such that they have their maximum curvature at the stimulation site.

3. The electrode arrangement of claim 2, wherein the polarity ratio is adjustable and/or is programmable by remote adjusting means.

4. The electrode arrangement of claim 1, wherein the electrodes of different polarity are disposed on the electrode line in such a way, and/or the ratio of the potentials is selected in such a way, and/or the ratio of the potentials is selected such is oriented at right angles to the heart wall.

5. The electrode arrangement of claim 1, wherein the electrodes of different polarity are disposed on the electrode line in such a way, and/or the ratio of the potentials is selected such that the resultant equipotential lines essentially enter the heart wall and emerge from it again at the stimulation site.

6. The electrode arrangement of claim 4, wherein the polarity ratio in favor of the negative proximal electrode in the atrium is essentially 4:1.

7. The electrode arrangement of claim 1, wherein the electrodes are disposed on the electrode line in such a way, and/or the ratio of the potentials is selected such that the effect on the phrenic nerve is minimal.

8. The electrode arrangement of claim 1, wherein the electrodes have a fractal surface.

9. The electrode arrangement of claim 1, wherein the stimulation site is the superior vena cava and/or the ventricle.

10. The electrode arrangement of claim 1, further comprising in a two-chamber electrode, an additional first and second electrode which are embodied in floating fashion and provided in the ventricle.

11. The electrode arrangement of claim 10, wherein the end intended for the stimulation in the ventricle has spacer means, instead of fixation means, which spacer means keep the first and second electrode, intended for the stimulation in the ventricle, centered in the region of the apex of the heart.

12. The electrode arrangement of claim 1, further comprising in a spatial relationship with the first and second electrodes, at least one additional electrode which is embodied and disposed in such a way and acted upon by a predetermined voltage.

13. The electrode arrangement of claim 1, wherein the second electrode and/or the at least one additional electrode are disposed in the intracardially placed electrode line.

14. The electrode arrangement of claim 12, wherein the electrode line is embodied such that the at least one additional electrode is disposed above the first and second electrodes.

15. The electrode arrangement of claim 12, wherein the electrode line is embodied such that the at least one additional electrode is disposed in the superior vena cava.

16. The electrode arrangement of claim 12, wherein the predetermined voltage is a second voltage pulse output essentially simultaneously with a first voltage pulse and having opposite polarity from the first voltage pulse; and that the potential gradient in the region of the sinoatrial node or the AV node rises beyond the value attainable with the first voltage pulse.

17. The electrode arrangement of claim 1, wherein the intracardially placed electrode line has a length and/or curvature dimensioned such that the first and second electrodes after introduction into the heart are disposed in the region of the roof of the atrium near the abouchement of the superior vena cava or near the septum and the abouchement of the coronary sinus into the atrium.

18. The electrode arrangement of claim 1, further comprising means actuatable from outside the body for varying the position of the first and second electrode after the electrode line has been introduced.

19. The electrode arrangement of claim 1, wherein the electrodes are disposed on the electrode arrangement, which is asymmetrical with respect to a center plane of the electrode line.

20. The electrode arrangement of claim 1, wherein the third electrode is embodied as a planar electrode disposed outside the heart, in the form of a housing for the cardiac pacemaker.

21. The electrode arrangement of claim 20, wherein the planar electrode is connected as an indifferent electrode.

22. The electrode arrangement of claim 1, wherein the electrode line has a group of four electrode segments, spaced apart from one another in the longitudinal direction of the electrode line, and the first voltage pulse is applied to the first and third or second and fourth electrode segments of the group, and the second pulse is applied to whichever electrode segments remain in the group.

* * * * *